(12) United States Patent
Raes et al.

(10) Patent No.: US 7,514,217 B2
(45) Date of Patent: Apr. 7, 2009

(54) MARKERS FOR ALTERNATIVELY ACTIVATED MACROPHAGES

(75) Inventors: Geert Raes, Sint-Genesius-Rode (BE); Gholamreza Hassanzadeh Ghassabeh, Watermaal-Bosvoorde (BE); Patrick De Baetselier, Berchem (BE)

(73) Assignees: Vlaams Interuniversitair Instituut voor Biotechnologie VZW, Zwijnaarde (BE); Vrije Universiteit Brussel, Brussel (BE)

( * ) Notice: Subject to any disclaimer, the term of this patent is extended or adjusted under 35 U.S.C. 154(b) by 279 days.

(21) Appl. No.: 11/371,784

(22) Filed: Mar. 9, 2006

(65) Prior Publication Data

US 2006/0183162 A1    Aug. 17, 2006

Related U.S. Application Data

(63) Continuation of application No. PCT/EP2004/052076, filed on Sep. 7, 2004.

(30) Foreign Application Priority Data

Sep. 9, 2003    (EP)    ................... 03102724

(51) Int. Cl.
  *C12Q 1/68*    (2006.01)
  *G01N 33/53*    (2006.01)
  *G01N 33/00*    (2006.01)

(52) U.S. Cl. ............................. 435/6; 435/7.1; 435/7.24

(58) Field of Classification Search ........................ None
  See application file for complete search history.

(56) References Cited

U.S. PATENT DOCUMENTS 5,527,884 A    6/1996    Russell et al.

FOREIGN PATENT DOCUMENTS

WO    WO 2005/024418    3/2005

OTHER PUBLICATIONS

Walter et al., J. Neurosci., 2004, 24: 8068-8074.*
Linehan et al., Laboratory Investigation, Aug. 2003, 83: 1223-1231.*
Imai et al., Restricted expression of galactose/N-acetylgalactosamine-specific macrophage C-type lectin to connective tissue and to metastatic lesion in mouse lung, Immunology, 1995, pp. 591-598, vol. 86.
PCT International Search Report, PCT/EP2004/052076, dated Mar. 11, 2005.
PCT Written Opinion of the International Searching Authority, PCT/EP2004/052076.
PCT International Preliminary Report on Patentability, PCT/EP2004/052076, dated Mar. 13, 2006.
Sato et al., Abstract, Molecular Cloning and Expression of cDNA Encoding a Galactose/N-Acetylgalactosamine-Specific Lectin on Mouse Tumoricidal Macrophages, Journal of Biochemistry, pp. 331-336, vol. 111, No. 3, Tokyo.
Suzuki et al., Abstract, Molecular cloning and expression of cDNA encoding human macrophage C-type lectin. Its unique carbohydrate binding specificity for Tn antigen, Journal of Immunology, pp. 128-135, vol. 156, No. 1, Baltimore, MD.
Linehan et al., Abstract, IL-4 receptor signaling is required for mannose receptor expression by macrophages recruited to granulomata but not resident cells in mice infected with *Schistosoma mansoni*, Laboratory Investigation, Aug. 2003, pp. 1223-1231, vol. 83, No. 8.
Loke et al., IL-4 dependent alternatively-activated macrophages have a distinctive in vivo gene expression phenotype, BMC Immunology, Jul. 4, 2002, pp. 1-11, vol. 3, No. 1.

* cited by examiner

*Primary Examiner*—Ilia Ouspenski
(74) *Attorney, Agent, or Firm*—TraskBritt

(57) ABSTRACT

The present invention relates to novel markers for alternatively activated macrophages. More specifically, the present invention relates to the use of galactose-type C-type lectins as surface markers that allows rapid identification and sorting of the alternative macrophages. Such identifications can be useful in diseases where there is an imbalance between proinflammatory and anti-inflammatory immune reactions.

6 Claims, 4 Drawing Sheets

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: mMGL1 sense primer

<400> SEQUENCE: 1
atgatgtctg ccagagaacc                                              20

<210> SEQ ID NO 2
<211> LENGTH: 22
<212> TYPE: DNA
<213> ORGANISM: Artificial Sequence
<220> FEATURE:
<223> OTHER INFORMATION: mMGL1 antisense primer

<400> SEQUENCE: 2
atcacagatt tcagcaacct ta                                           22
```

<210> SEQ ID NO 3
<211> LENGTH: 21
<212> TYPE: DNA
<213> ORGANISM: Artificial Sequence
<220> FEATURE:
<223> OTHER INFORMATION: mMGL2 sense primer

<400> SEQUENCE: 3
gataactggc atggacatat g                                           21

<210> SEQ ID NO 4
<211> LENGTH: 23
<212> TYPE: DNA
<213> ORGANISM: Artificial Sequence
<220> FEATURE:
<223> OTHER INFORMATION: mMGL2 antisense primer

<400> SEQUENCE: 4
tttctaatca ccataacaca ttc                                         23

<210> SEQ ID NO 5
<211> LENGTH: 21
<212> TYPE: DNA
<213> ORGANISM: Artificial Sequence
<220> FEATURE:
<223> OTHER INFORMATION: mouse arginase-1 sense primer

<400> SEQUENCE: 5
atggaagaga ccttcagcta c                                           21

<210> SEQ ID NO 6
<211> LENGTH: 21
<212> TYPE: DNA
<213> ORGANISM: Artificial Sequence
<220> FEATURE:
<223> OTHER INFORMATION: mouse arginase-1 antisense primer

<400> SEQUENCE: 6
gctgtcttcc caagagttgg g                                           21

<210> SEQ ID NO 7
<211> LENGTH: 20
<212> TYPE: DNA
<213> ORGANISM: Artificial Sequence
<220> FEATURE:
<223> OTHER INFORMATION: human arginase 1 antisense

<400> SEQUENCE: 7
agtccgaaac aagccaaggt                                             20

<210> SEQ ID NO 8
<211> LENGTH: 24
<212> TYPE: DNA
<213> ORGANISM: Artificial Sequence
<220> FEATURE:
<223> OTHER INFORMATION: mouse ribosomal protein S12 antisense

<400> SEQUENCE: 8
ggaaggcata gctgctggag gtgt                                        24

<210> SEQ ID NO 9
<211> LENGTH: 20
<212> TYPE: DNA
<213> ORGANISM: Artificial Sequence
<220> FEATURE:
<223> OTHER INFORMATION: mouse MMR (Mrc1) sense

<400> SEQUENCE: 9
ctcgtggatc tccgtgacac                          20

<210> SEQ ID NO 10
<211> LENGTH: 20
<212> TYPE: DNA
<213> ORGANISM: Artificial Sequence
<220> FEATURE:
<223> OTHER INFORMATION: mouse MMR (Mrc1) antisense

<400> SEQUENCE: 10
gcaaatggag ccgtctgtgc                          20

<210> SEQ ID NO 11
<211> LENGTH: 20
<212> TYPE: DNA
<213> ORGANISM: Artificial Sequence
<220> FEATURE:
<223> OTHER INFORMATION: human ribosomal protein S12 sense

<400> SEQUENCE: 11
gaattcgcga agctgccaaa                          20

<210> SEQ ID NO 12
<211> LENGTH: 20
<212> TYPE: DNA
<213> ORGANISM: Artificial Sequence
<220> FEATURE:
<223> OTHER INFORMATION: human ribosomal protein S12 antisense

<400> SEQUENCE: 12
gactccttgc catagtcctt                          20

<210> SEQ ID NO 13
<211> LENGTH: 19
<212> TYPE: DNA
<213> ORGANISM: Artificial Sequence
<220> FEATURE:
<223> OTHER INFORMATION: hMGL sense

<400> SEQUENCE: 13
cctcagtgac cctgaagga                           19

<210> SEQ ID NO 14
<211> LENGTH: 20
<212> TYPE: DNA
<213> ORGANISM: Artificial Sequence
<220> FEATURE:
<223> OTHER INFORMATION: hMGL antisense

<400> SEQUENCE: 14
aaaggcagct cagtgactct                          20

<210> SEQ ID NO 15
<211> LENGTH: 20
<212> TYPE: DNA
<213> ORGANISM: Artificial Sequence
<220> FEATURE:
<223> OTHER INFORMATION: human MMR (Mrc1) sense

<400> SEQUENCE: 15
cctctggtga acggaatgat                          20

<210> SEQ ID NO 16

```
<211> LENGTH: 20
<212> TYPE: DNA
<213> ORGANISM: Artificial Sequence
<220> FEATURE:
<223> OTHER INFORMATION: human MMR (Mrc1) antisense

<400> SEQUENCE: 16
aggccagcac ccgttaaaat                                              20

<210> SEQ ID NO 17
<211> LENGTH: 20
<212> TYPE: DNA
<213> ORGANISM: Artificial Sequence
<220> FEATURE:
<223> OTHER INFORMATION: human arginase 1 sense

<400> SEQUENCE: 17
ggcaaggtga tggaagaaac                                              20

<210> SEQ ID NO 18
<211> LENGTH: 24
<212> TYPE: DNA
<213> ORGANISM: Artificial Sequence
<220> FEATURE:
<223> OTHER INFORMATION: mouse ribosomal protein S12 sense

<400> SEQUENCE: 18
cctcgatgac atccttggcc tgag                                         24
```

MARKERS FOR ALTERNATIVELY ACTIVATED MACROPHAGES

CROSS-REFERENCE TO RELATED APPLICATIONS

This application is a continuation of PCT International Patent Application No. PCT/EP2004/052076, filed on Sep. 7, 2004, designating the United States of America, and published, in English, as PCT International Publication No. WO 2005/024418 A2 on Mar. 17, 2005, which application itself claims priority to European Patent Application Serial No. 03102724.6 filed on Sep. 9, 2003, the contents of the entirety of each of which are hereby incorporated herein by this reference.

TECHNICAL FIELD

The present invention relates generally to biotechnology and, more particularly, to novel markers for alternatively activated macrophages. More specifically, the present invention relates to the use of galactose-type C-type lectins as surface markers that allows rapid identification and sorting of the alternative macrophages. Such identifications can be useful in diseases where there is an imbalance between proinflammatory and anti-inflammatory immune reactions.

BACKGROUND

Primarily due to differences in the cytokine environments to which macrophages are exposed, these can develop into different subsets exhibiting different functional and molecular properties (Goerdt and Orfanos, 1999; Gordon, 2000). The best-studied macrophage subsets are classically activated macrophages (caMF), differentiating in the presence of stimuli such as IFN-γ and LPS and being important components of host defense in the fight against various pathogens. On the other hand, type II cytokines such as IL-4 and IL-13, antagonize caMF and induce the development of alternatively activated macrophages (aaMF). The latter are considered to secure the balance between pro- and anti-inflammatory reactions during type I cytokine-driven inflammatory responses and to be involved in angiogenesis and wound healing (Goerdt and Orfanos, 1999). However, the association of aaMF with type II cytokine-controlled inflammatory diseases (Loke et al., 2000) suggests that, under these circumstances, aaMF may support the development of pathology. To gain better insights into the exact functional properties of aaMF in vivo, there is an urgent requirement for better and additional markers for (in situ) analysis of aaMF, as well as for FACS analysis of isolated cells. Discrimination between murine caMF and aaMF has so far been based mainly on differential arginine metabolism. Hence, in caMF, L-arginine is converted in NO and L-citrulline via inducible nitric oxide synthase (iNOS), whereas aaMF are characterized by an alternative metabolic pathway of arginine, catalyzed by arginase 1, converting L-arginine to L-ornithine and urea.

Recently, several new markers have been described. Gratchev et al. (2001) applied an in vitro approach, using a combination of subtractive hybridization and differential hybridization with IL-4- or IF-γ-stimulated macrophages, and found that fibronectin and the extracellular matrix protein βIG-H3 are differentially expressed. However, the in vitro stimulation may lead to artifacts. Therefore, Raes et al. (2002) used suppression subtraction hybridization in an in vivo experimental model of murine trypanosomosis to identify genes that are differentially expressed in aaMF versus caMF, and identified the secreted factors FIZZ1 and Ym as possible markers. Loke et al. (2002) constructed a subtractive library from purified peritoneal macrophages from *Brugia malayi*-implanted WT mice against peritoneal macrophages of IL-4$^{-/-}$ mice infected with *B. malayi*, and identified several possible marker genes, including the previously in vivo-identified FIZZ1 and Ym, but not the in vitro-identified markers.

Notwithstanding these newly identified marker genes, there is still a need for an easily identifiable marker. Surprisingly, we found that galactose C-type lectins 1 and 2 are also differentially expressed between aaMF and caMF. As these markers are situated on the cell membrane, they allow non-destructive recognition of the aaMF. Moreover, contrary to secreted markers, they allow, for the first time, a reliable sorting and purification of the aaMF fraction.

DISCLOSURE OF THE INVENTION

A first aspect of the invention is the use of the MGL gene expression level as a marker for alternatively activated macrophages. MGL genes have been described in humans (Genbank accession number NP_878910 and NP_006335), rat (Genbank accession number P49301) and mice (Genbank accession number AAHA4811 and NP-660119). The Genbank numbers are cited as non-limiting examples of MGL genes. Preferably, MGL is human MGL isoform 1, human MGL isoform 2, mouse MGL1 or mouse MGL2. Methods to measure the expression level are known to the person skilled in the art and include, but are not limited to, DNA-RNA hybridization and PCR-related methods, using primers specific for the MGL messenger RNA. Alternatively, the expression level may be measured at the level of the protein, using, as a non-limiting example, antibody-based techniques such as ELISA. Still another way to measure the expression level is by the use of a reporter gene, operably linked to the MGL promoter. "Operably linked" refers to a juxtaposition wherein the components so described are in a relationship permitting them to function in their intended manner. A promoter sequence operably linked to a coding sequence is ligated in such a way that expression of the coding sequence is achieved under conditions compatible with the promoter sequence. Alternatively, the reporter gene is fused to a coding sequence of MGL and expressed as a fusion protein, comprising a part of the MGL amino acid sequence up to the total sequence. Suitable reporter genes are known to the person skilled in the art and include, but are no limited to, antibiotic resistance genes, genes encoding fluorescent proteins, or genes encoding surface markers.

Increased expression of human MGL is leading to synthesis of galactose-type C-type lectin; increased expression of mouse MGL1 and/or MGL2 is leading to synthesis of galactose-type C-type lectin 1 and or galactose-type C-type lectin 2. Therefore, another aspect of the invention is the use of a galactose-type C-type lectin, preferably human galactose-type C-type lectin isoform 1, human galactose-type C-type isoform 2, murine lectin galactose-type C-type lectin 1 and/or murine galactose-type C-type lectin 2 as marker for alternatively activated macrophages.

Still another aspect of the invention is the use of a cell surface marker for sorting of alternatively activated macrophages. Indeed, the present reliable markers are either intracellular (like arginase) or secreted (like FIZZ1 and Ym). Extracellular matrix proteins like fibronectin or βIG-H3 may not be specific enough to allow sorting of the aaMF fraction.

Preferably, the cell surface marker is a galactose-type C-type lectin. Even more preferably, the cell surface marker is chosen from the group consisting of human galactose-type C-type lectin isoform 1, human galactose-type C-type isoform 2, murine lectin galactose-type C-type lectin 1 and murine galactose-type C-type lectin 2.

Still another aspect of the invention is the use of the MGL gene expression level, or the use of a galactose-type C-type lectin for diagnosis or theranosis of a disease. Preferably, the use is for theranosis. Preferably, the MGL is chosen from the group consisting of human MGL isoform 1, human MGL isoform 2, mouse MGL1 and mouse MGL2. Preferably, the galactose-type C-type lectin is chosen from the group consisting of human galactose-type C-type lectin isoform 1, human galactose-type C-type isoform 2, murine lectin galactose-type C-type lectin 1 and murine galactose-type C-type lectin 2.

Preferably, the disease is a disease where there is an imbalance between proinflammatory and anti-inflammatory immune reactions. Even more preferably, the disease is allergic asthma, rheumatoid arthritis, cancer, trypanosomosis, leprosis, helminthiasis or graft versus host disease. Indeed, it is known that aaMF are found in Th2-mediated inflammatory settings. In addition, alternatively activated macrophages are the cells of origin in cutaneous macrophage-derived tumors, and may have an angiogenic effect, which is also promoting tumor growth. Diagnosis or theranosis of the aaMF population can hold to identify and treat the disease. "Theranosis" as used herein is a diagnostic method, wherein the results are used to follow the evolution of the disease, to evaluate the efficacy of the medication and/or to adapt the treatment in function of the result of the diagnosis. As the marker allows following the evolution of the aaMF population during the treatment, it allows for the first time theranosis in those diseases where there is an imbalance in macrophage populations.

DETAILED DESCRIPTION OF THE INVENTION

Figure 1:
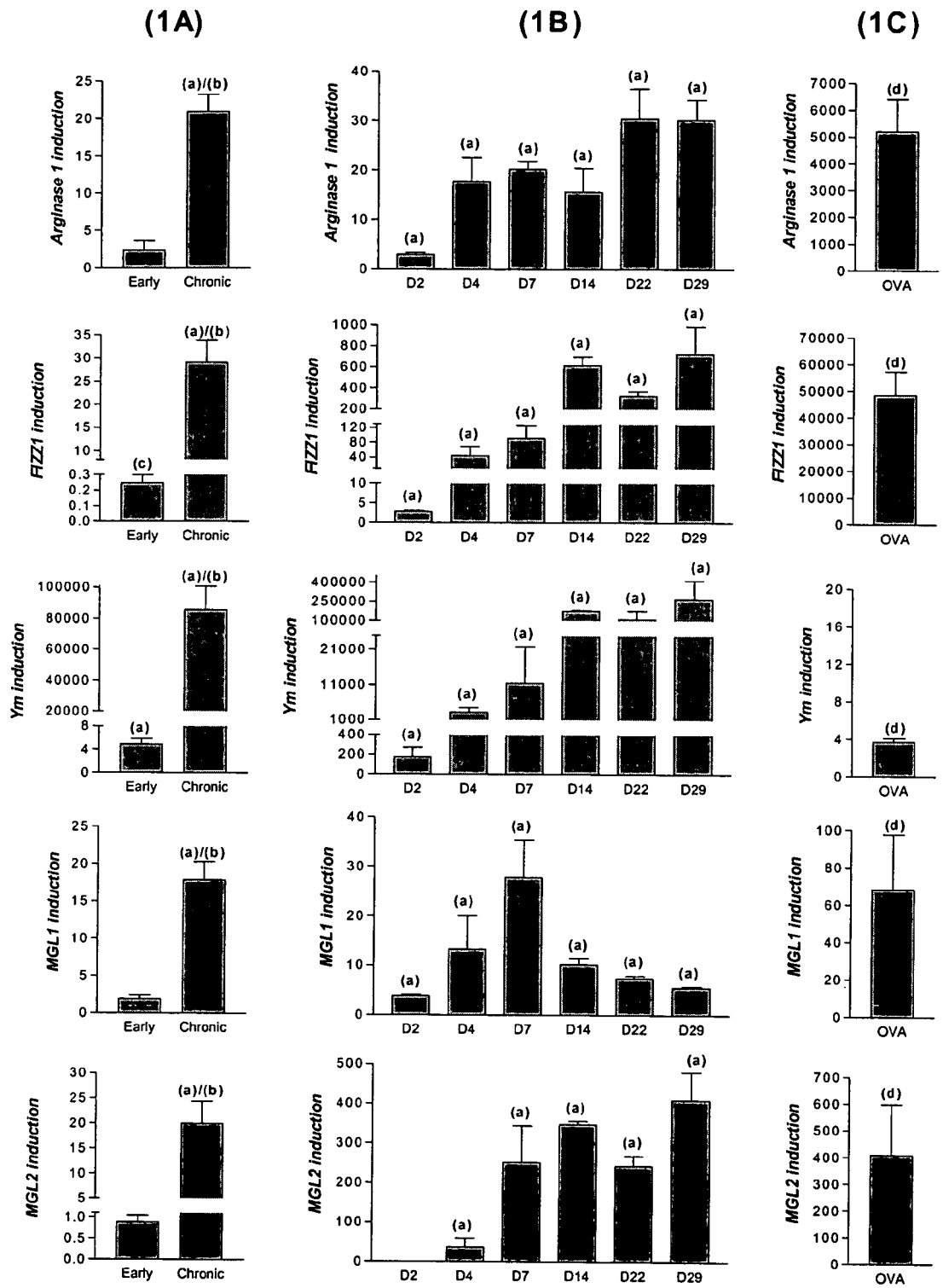
FIG. 1: In vivo modulation of arginase 1, FIZZ1, Ym, MGL1 and MGL2 expression. Gene expression was determined via quantitative RT-PCR and has been normalized for the housekeeping gene ribosomal protein S12. Column 1A: Fold induction of the genes in plastic-adherent peritoneal macrophages from $PLC^{-/-}$ $Tb.$ $brucei$-infected F1 mice at the early (caMF) or chronic stage (aaMF) of infection, as compared to non-infected mice; Column 1B: Fold induction of the genes in plastic-adherent peritoneal macrophages from $Taenia$ $crassiceps$-infected BALB/c mice at 2, 4, 7, 14, 22 and 29 days post-infection, as compared to non-infected mice; Column 1C: Fold induction of the genes in alveolar macrophages from OVA-challenged (aaMF) C57bl/6 mice, as compared to non-challenged control mice. (a): significantly higher than non-infected ($p<0.05$); (b): significantly higher than early ($p<0.05$); (c): significantly lower than non-infected ($p<0.05$); (d): significantly higher than no challenge ($p<0.05$).

The invention is further explained with the aid of the following illustrative Examples.

EXAMPLES

Material and Methods to the Examples

In vivo Models and Preparation of Macrophage Populations

F1 (C57B1/6×BALB/c) mice were infected with $PLC^{-/-}$ $T.$ $b.$ $brucei$ (Namangala et al., 2001) and Balb/c with Toi strain $Taenia$ $crassiceps$ metacestodes as described (Rodriguez-Sosa et al., 2002). Isolation of plastic-adherent peritoneal macrophages from infected animals and generation and in vitro cytokine stimulation of thioglycollate-elicited macrophages were as described (Raes et al., 2002). After induction of airway inflammation in C57B1/6 mice (Pynaert et al., 2003) and collection of bronchoalveolar lavage fluid (Pynaert et al., 2003), alveolar macrophages were first enriched via a Dynal (Oslo, Norway) magnetic particle concentrator, using CELLection Dynabeads and CD11 c antibodies (Pharmingen, San Diego, Calif.), followed by fluorescence-activated sorting of high-autofluorescent cells.

In vitro Cytokine Treatment of Murine Macrophages and Human Monocytes

The plastic-adherent population of PEC from BALB/c mice, injected intraperitoneally with 3 ml thioglycollate broth (BioMérieux, Marcy l' Etoile, France) four days prior to collection, was cultured in the presence of 100 IU/ml mouse recombinant IL-4 (Pharmingen) or 100 IU/ml mouse recombinant IFN-γ (Pharmingen) for 48 hours.

Human peripheral blood monocytes were prepared as previously described (Vanham et al., 2000). Briefly, PBMC isolated from donor buffy coats were separated into lymphocyte- and monocyte-enriched fractions by counter-flow elutriation. The pooled monocyte-enriched fractions were treated with sheep erythrocytes, after which the E-rosette-negative fraction was obtained using density gradient separation. $6 \times 10^6$ cells were dispensed in six-well tissue culture dishes (Falcon) in 3 ml RPMI 1640 medium supplemented with 10% heat-inactivated fetal calf serum, 2 mM L-glutamine, 100 IU/ml penicillin and 100 μg/ml streptomycin (Gibco-Invitrogen) and incubated in vitro for three days with human recombinant IFN-γ (1000 IU/ml) or human recombinant IL-4 (15 ng/ml) at 37° C. in a humidified incubator containing 5% $CO_2$ in air.

RNA Extraction and Quantitative Reverse-Transcription Polymerase Chain Reaction (RT-PCR) Analysis After preparation of total RNA and cDNA (Raes et al., 2002), quantitative real-time PCR was performed in a Bio-Rad (Hercules, Calif.) icycler, with Bio-Rad iQ SYBR Green Supermix. Primers and PCR conditions were as described before for mouse FIZZ1 and Ym (Raes et al. 2002) and for human AMAC-1 (Kodelja et al. 1998). Other primers used were: mouse ribosomal protein S12 sense (5'-CCTCGATGA-CATCCTTGGCCTGAG-3') (SEQ ID NO:18), mouse ribosomal protein S12 antisense (5'-GGAAGGCATAGCT-GCTGGAGGTGT-3') (SEQ ID NO:8), mMGL1 sense (5'-ATGATGTCTGCCAGAGAACC-3') (SEQ ID NO:1), mMGL1 antisense (5'-ATCACAGATTTCAGCAACCTTA-3') (SEQ ID NO:2), mMGL2 sense (5'-GATAACTGGCATG-GACATATG-3') (SEQ ID NO:3), mMGL2 antisense (5'-TTTCTAATCACCATAACACATTC-3') (SEQ ID NO:4), mouse MMR (Mrc1) sense (5'-CTCGTGGATCTCCGTGA-CAC-3') (SEQ ID NO:9), mouse MMR (Mrc1) antisense (5'-GCAAATGGAGCCGTCTGTGC-3') (SEQ ID NO:10), mouse arginase 1 sense (5'-ATGGAAGAGACCTTCAGC-TAC-3') (SEQ ID NO:5), mouse arginase 1 antisense (5'-GCTGTCTTCCCAAGAGTTGGG-3') (SEQ ID NO:6), human ribosomal protein S12 sense (5'-GAATTCGC-GAAGCTGCCAAA-3') (SEQ ID NO:11), human ribosomal protein S12 antisense (5'-GACTCCTTGCCATAGTCCTT-3') (SEQ ID NO:12), hMGL sense (5'-CCTCAGTGACCCT-GAAGGA-3') (SEQ ID NO:13), hMGL antisense (5'-AAAGGCAGCTCAGTGACTCT-3') (SEQ ID NO:14), human MMR (Mrc1) sense (5'-CCTCTGGTGAACGGAAT-GAT-3') (SEQ ID NO:15), human MMR (Mrc1) antisense (5'-AGGCCAGCACCCGTTAAAAT-3') (SEQ ID NO:16), human arginase 1 sense (5'-GGCAAGGTGATGGAA-GAAAC-3') (SEQ ID NO:17) and human arginase 1 antisense (5'-AGTCCGAAACAAGCCAAGGT-3') (SEQ ID NO:7). For all these primers, each PCR cycle consisted of 1 minute denaturation at 94° C., 45 seconds annealing at 55° C. and 1 minute extension at 72° C. Gene expression was normalized using ribosomal protein S12 as housekeeping gene. Similar results were obtained using other housekeeping genes.

Statistical Analysis

All comparisons were tested for statistical significance ($p<0.05$) using the unpaired t test.

Example 1

Identification of MGL2 from the SSH Library

One of the clones picked up from the SSH library contained a fragment of MGL2, a recently identified macrophage C-type lectin with a high homology (91.5% amino acid identity) but a distinct carbohydrate specificity from the originally identified MGL, which has now been called MGL1 (Tsuiji et al., 2002). MGL(1) was found to be mainly restricted to macrophages in connective tissues (Imai et al., 1995) and to act as recognition molecule for glycosylated antigens on cancer cells (Ichii et al., 2000). Human MGL, for which so far one gene locus but several mRNA species, apparently derived from alternative splicing, were identified (Higashi et al., 2002), was shown to recognize Tn antigen, a carcinoma-associated epitope, consisting of a cluster of serine or threonine-linked N-acetylgalactosamine (Suzuki et al., 1996). Recent studies demonstrated that both human and mouse MGL are expressed by immature dendritic cells and are involved in the uptake of glycosylated antigens (Higashi et al., 2002; Denda-Nagai et al., 2002).

Example 2

MGL1 and MGL2 Expression in aaMF Elicited During $PLC^{-/-}$ *T. b. brucei* infection To analyze the expression of MGL1 and MGL2 in caMF and aaMF, quantitative RT-PCR was first performed on RNA from peritoneal macrophages elicited via the $PLC^{-/-}$ *T. b. brucei* model used to generate the SSH library. In this model, correlating with a switch from a type I cytokine environment in the early stage of infection to a type II cytokine environment in the late and chronic phases, macrophages from early stage infected mice are caMF, while those from the late and chronic stages of infection are aaMF (Namangala et al., 2001). MGL1 and MGL2, similar to arginase 1, FIZZ1 and Ym, were found to be significantly induced in plastic-adherent peritoneal exudate cells (PECs) from chronic stage $PLC^{-/-}$ *T. b. brucei*-infected F1 mice (aaMF) as compared to early stage infected (caMF) or non-infected mice (FIG. 1, Column 1A). Similar results were obtained in peritoneal macrophages purified from PECs via FACS sorting, indicating that the observed modulations of gene expression are not due to the plastic adherence procedure.

Example 3

Distinct Kinetics of MGL1 and MGL2 Modulation during *Taenia crassiceps* Infections Infections with Helminths such as *Taenia crassiceps* are characterized by a gradual progression to polarized type II immune responses and the generation of aaMF (Rodriguez-Sosa et al., 2002). As shown in FIG. 1, Column 1B, the pattern of MGL2 induction in peritoneal macrophages during infection with *T. crassiceps* is similar to arginase 1, FIZZ1 and Ym, with a gradual increase in expression until a plateau is reached a few weeks after inoculation. Although MGL1 is also induced during *T. crassiceps* infection, its induction level as compared to non-infected animals never reaches the several 100-fold observed for MGL2 and the pattern of induction is quite distinct: a gradual increase in the first week of infection, after which the induction level falls back to five- to ten-fold. These differences suggest MGL1 and MGL2 may exert distinct functions in vivo.

Example 4

MGL2 and MGL1 Induction in Alveolar aaMF

To examine whether the enhanced expression of MGL1 and MGL2 in aaMF occurs in macrophage populations besides peritoneal macrophages and in disease models besides parasite infections, allergic, type II cytokine-dependent pulmonary inflammation was induced in sensitized mice using ovalbumin (OVA) aerosols and alveolar macrophages were purified from bronchoalveolar lavage (BAL) fluid. These alveolar aaMF were characterized by a high induction of both MGL1 and MGL2 as compared to alveolar macrophages from control animals, wherein the induction level was more pronounced for MGL2 than MGL1 (FIG. 1, Column 1C). On the other hand, MGL2, but not MGL1, expression was dramatically reduced in alveolar macrophages from mice with experimental type I inflammation, induced via intratracheal administration of LPS. An LPS-induced reduction of gene expression was also observed for FIZZ1 (FIG. 1, Column 1C).

Example 5

Figure 2:
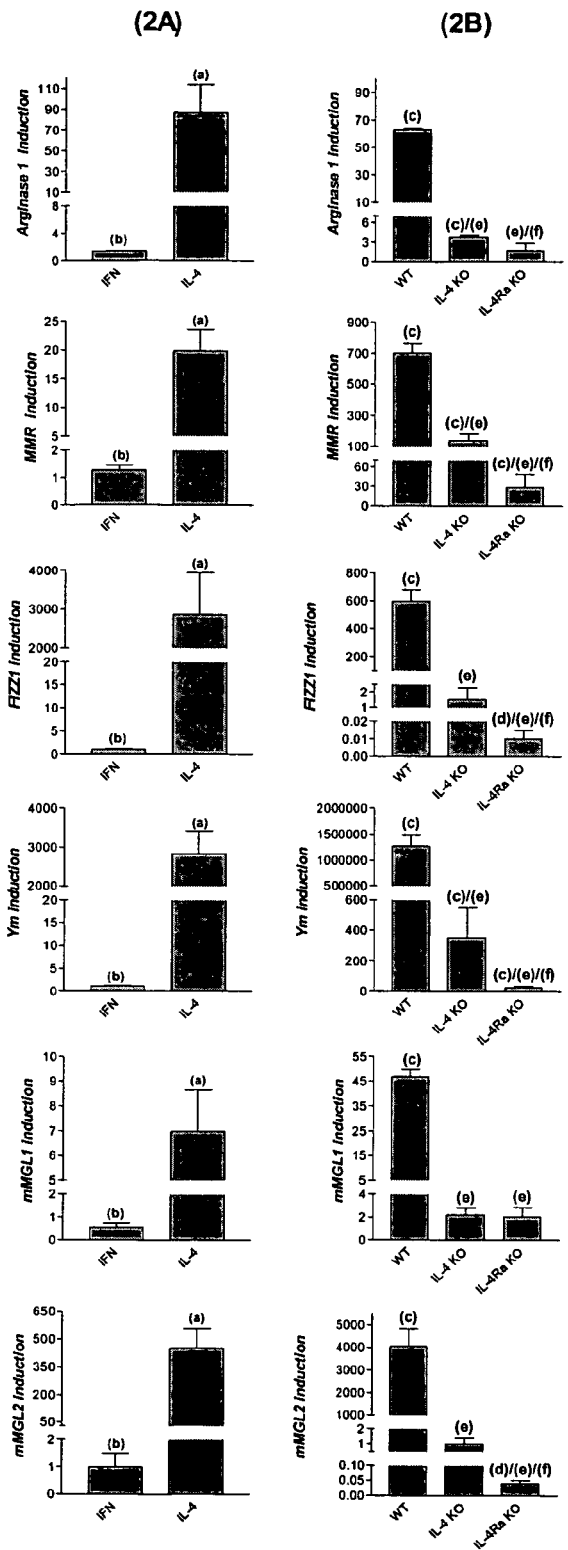
FIG. 2: In vitro cytokine modulation and in vivo dependence on cytokine signaling of arginase 1, MMR, FIZZ1, Ym, mMGL1 and mMGL2 expression. Data are shown for one representative experiment. Gene expression was determined via quantitative RT-PCR and has been normalized for the housekeeping gene ribosomal protein S12. Column 2A: Fold induction of the genes in thioglycollate-elicited peritoneal macrophages, incubated in vitro for 48 hours in the presence of IFN-γ or IL-4, as compared to the no treatment control (incubated in vitro in the absence of cytokines); Column 2B: Fold induction of the genes in peritoneal macrophages from $Taenia$ $crassiceps$-infected wild-type (wt), IL-4-deficient (IL-4 KO) or IL-4Rα-deficient (IL-4Ra KO) BALB/c mice at 32 days post-infection, as compared to non-infected mice. (a): significantly higher than no treatment ($p<0.05$); (b): significantly lower than IL-4 treatment ($p<0.05$); (c): significantly higher than non-infected ($p<0.05$); (d): significantly lower than non-infected ($p<0.05$); (e): significantly lower than infected wt mice ($p<0.05$); (f): significantly lower than infected IL-4 KO mice ($p<0.05$). The error bars indicate the standard error of the mean.

In vitro Cytokine Modulation and in vivo Dependence on Cytokine Signaling of mMGL1 and mMGL2 Expression To verify the association of mMGL1 and mMGL2 with type II cytokine-induced aaMF, thioglycollate-elicited peritoneal macrophages were incubated with the type II cytokines IL-4 or IL-13. Both cytokines moderately induced mMGL1 expression and strongly induced mMGL2 expression (FIG. 2, Column 2A). A similar behavior was observed for the previously identified aaMF markers arginase 1, MMR, FIZZ 1 and Ym.

To investigate the contribution of type II cytokines to the in vivo induction of the expression of these markers, *T. crassiceps* infections were performed in wild-type (wt), IL-4-deficient (IL-4 KO) and IL-4Rα-deficient (IL-4Rα KO) BALB/c mice. In peritoneal macrophages from non-infected animals, no significant differences were detected in the expression levels of arginase 1, MMR, FIZZ1, Ym, mMGL1 or mMGL2 between the three types of mice. Also, upon *T. crassiceps* infection of the three types of mice, a similar parasite burden was recorded up to the time when peritoneal macrophages were isolated. Yet, induction of mMGL1 and mMGL2, similar to arginase 1 and FIZZ1, was marginal or not significant in IL-4 KO as compared to wt mice during infection (FIG. 2, Column 2B). Although the in vivo induction of Ym and MMR was also drastically reduced in the absence of IL-4, a significant induction of these two genes was still recorded in infected IL-4 KO mice. This residual induction of MMR and Ym may be due to IL-13 signaling, since their fold of induction was further reduced in IL-4Rα KO mice, lacking both IL-4 and IL-13 signaling (Murata et al., 1999). Hence, in this infection model, expression of this set of aaMF markers, including the novel mMGL1 and mMGL2 markers, requires IL-4 receptor-mediated signaling. This is in accordance with what has been documented before for arginase 1 (Hesse et al., 2001) and MMR (Linehan et al., 2003) during *Schistosoma mansoni* infection and for FIZZ1 and Ym during trypanosome infections (Raes et al., 2002).

Example 6

Detection of the aaMF Fraction in Helminth-Infected Mice

Figure 3:
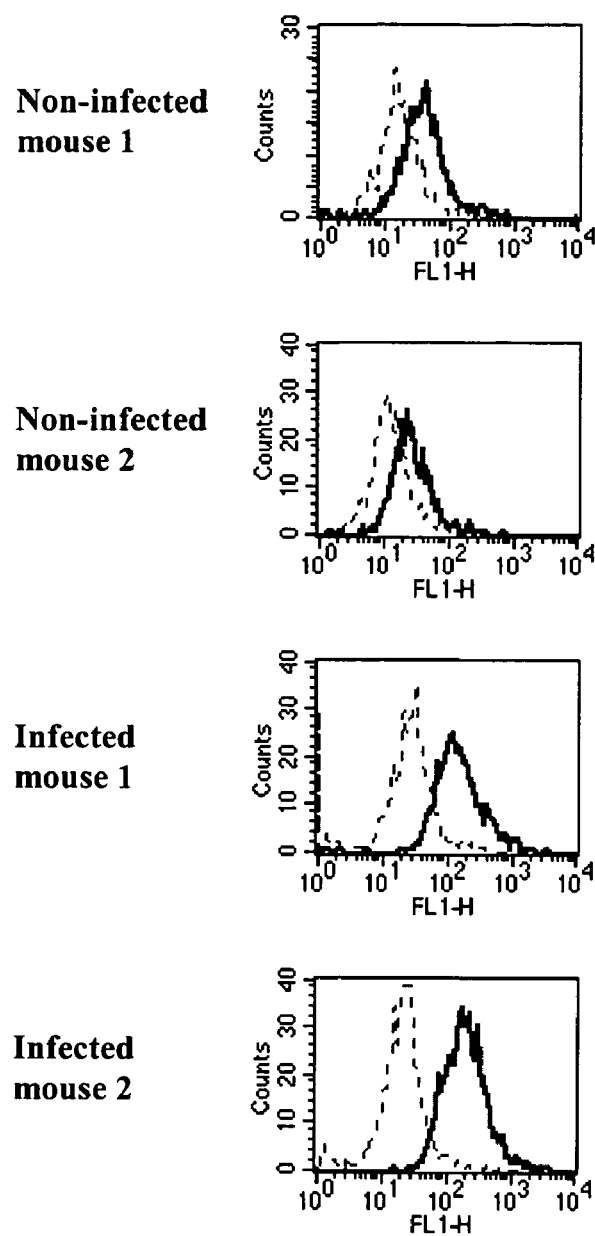
FIG. 3: Expression of MGL on peritoneal macrophages from $Taenia$-$crassiceps$-infected mice at three weeks post-infection. Expression was determined by direct immunofluorescence and FACS analysis. Total cells from peritoneal lavage were stained with PE-labeled anti-F4/80 antibodies and either FITC-labeled ER-MP23 anti-MGL antibodies or FITC-labeled isotype-matched control antibodies. Expression profiles are shown for gated F4/80-positive mature macrophages. The profiles represent the distribution of fluorescent cells in function of fluorescence intensity in the FITC channel of the flow cytometer. The dotted peak corresponds to the background profile of cells stained with the FITC-labeled isotype-matched control antibody. Similar results were obtained at different time points post-infection. Results are shown for one out of three independent experiments.

After having established that MGL mRNA is induced in alternatively activated macrophages in vivo and in vitro, we wanted to assess if alternative activation of macrophages was also associated with an enhanced surface expression of MGL and, hence, whether this lectin would represent a useful surface marker for alternatively activated macrophages. To this aim, expression of MGL was tested on peritoneal macrophages from mice infected with the Helminth *Taenia crassiceps*. MGL was detected by the MGL-specific antibody ER-MP23 (BMA biomedicals AG; Leenen et al., 1994) that is described as specific for macrophages of connective tissue in mice. As shown in FIG. 3, alternatively activated macrophages exhibited increased expression of MGL, as compared to a low basal expression in peritoneal macrophages from non-infected mice.

Example 7 hMGL as Marker for Human IL-4-Elicited aaMF

As is the case in murine aaMF, expression of MMR was reported to be induced in human aaMF (McNally et al., 1996). Yet, for FIZZ1 and Ym, so far, no human homologues associated with alternative activation of macrophages have been described and also human arginase 1 has not been documented as a marker for aaMF. On the other hand, using comparative gene expression profiling of human peripheral blood monocytes incubated in vitro with IL-4 versus IFN-γ, expression of certain genes, with AMAC-1 (alternative macrophage activation-associated CC-chemokine-1) as most promising example, has been identified to be associated with alternative activation of human macrophages (Kodelja et al., 1998). Yet no murine homologue of AMAC-1, acting as a marker for aaMF, has currently been defined.

Figure 4:
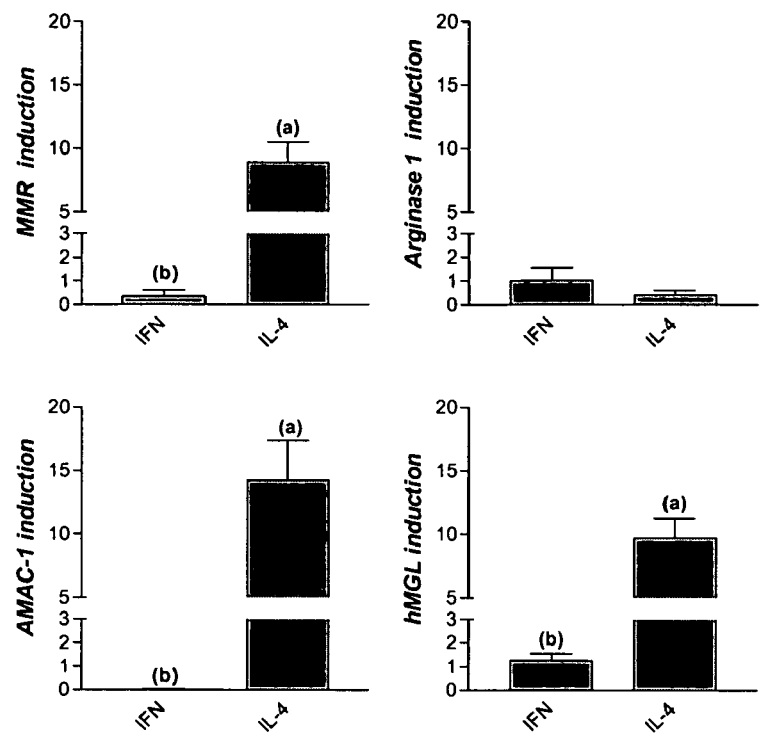
FIG. 4: In vitro cytokine modulation of MMR, arginase 1, AMAC-1 and hMGL expression in human monocytes. Fold induction of the genes in peripheral blood monocytes, incubated in vitro for three days in the presence of IFN-γ or IL-4, as compared to the no treatment control (incubated in vitro in the absence of cytokines). Data are shown for one representative experiment. Gene expression was determined via quantitative RT-PCR and has been normalized for the housekeeping gene ribosomal protein S12. (a): significantly higher than no treatment ($p<0.05$); (b): significantly lower than IL-4 treatment ($p<0.05$). The error bars indicate the standard error of the mean.

To analyze if human MGL (hMGL), for which so far only one single gene locus has been identified (Higashi et al., 2002), is acting as a marker for human aaMF, human peripheral blood monocytes were treated in vitro with IL-4 or IFN-γ. Similar to human MMR and AMAC-1, but unlike human arginase 1, hMGL expression in monocytes was significantly induced by IL-4, but not by IFN-γ (FIG. 4).

REFERENCES

1. Denda-Nagai K., N. Kubota, M. Tsuiji, M. Kamata, and T. Irimura. Macrophage C-type lectin on bone marrow-derived immature dendritic cells is involved in the internalization of glycosylated antigens. *Glycobiology* 2002; 12:443-450.
2. Goerdt S. and C. E. Orfanos. Other functions, other genes: alternative activation of antigen-presenting cells. *Immunity* 1999; 10:137-142.
3. Gordon S. Alternative activation of macrophages. *Nat. Rev. Immunol.* 2003; 3:23-35.
4. Gratchev A., P. Guillot, N. Hakiy, O. Politz, C. E. Orfanos, K. Schledzewski, and S. Goerdt. Alternatively activated macrophages differentially express fibronectin and its splice variants and the extracellular matrix protein βIG-H3. *Scand. J. Immunol.* 2001; 52:386-392.
5. Hesse M., M. Modolell, A. C. La Flamme, M. Schito, J. M. Fuentes, A. W. Cheever, E. J. Pearce, and T. A. Wynn. Differential regulation of nitric oxide synthase-2 and arginase-1 by type 1/type 2 cytokines in vivo: granulomatous pathology is shaped by the pattern of L-arginine metabolism. *J. Immunol.* 2001; 167, 6533-6544.
6. Higashi N., K. Fujioka, K. Denda-Nagai, S. Hashimoto, S. Nagai, T. Sato, Y. Fujita, A. Morikawa, M. Tsuiji, M. Miyata-Takeuchi, Y. Sano, N. Suzuki, K. Yamamoto, K. Matsushima, and T. Irimura. The macrophage C-type lectin specific for galactose/N-acetylgalactosamine is an endocytic receptor expressed on monocyte-derived immature dendritic cells. *J. Biol. Chem.* 2002; 277:20686-20693.
7. Ichii S., Y. Imai, and T. Irimura. Initial steps in lymph node metastasis formation in an experimental system: possible involvement of recognition by macrophage C-type lectins. *Cancer Immunol. Immunother.* 2000; 49:1-9.
8. Imai Y., Y. Akimoto, S. Mizuochi, T. Kimura, H. Hirano, and T. Irimura. Restricted expression of galactose/N-acetylgalactosamine-specific macrophage C-type lectin to connective tissue and to metastatic lesions in mouse lung. *Immunology* 1995; 86:591-598.
9. Kodelja V., C. Muller, O. Politz, N. Hakij, C. E. Orfanos, and S. Goerdt. Alternative macrophage activation-associated CC-chemokine-1, a novel structural homologue of macrophage inflammatory protein-1 alpha with a Th2-associated expression pattern. *J. Immunol.* 1998; 160, 1411-1418.
10. Leenen P. J., M. F. de Bruijn, J. S. Voerman, P. A. Campbell, and W. van Ewijk. Markers of mouse macrophage development detected by monoclonal antibodies. *J. Immunol. Methods* 1994; 174, 5-19.
11. Linehan S. A., P. S. Coulson, R. A. Wilson, A. P. Mountford, F. Brombacher, L. Martinez-Pomares, and S. Gordon. IL-4 receptor signaling is required for mannose receptor expression by macrophages recruited to granulomata but not resident cells in mice infected with *Schistosoma mansoni*. *Lab. Invest.* 2003; 83, 1223-1231.
12. Loke P., A. S. MacDonald, and J. E. Allen. Antigen-presenting cells recruited by *Brugia malayi* induce Th2 differentiation of naive CD4(+) T cells. *Eur. J. Immunol.* 2000; 30:1127-1135.
13. Loke P., M. G. Nair, J. Parkinson, D. Guiliano, M. Blaxter, and J. E. Allen. IL-4 dependent alternatively-activated macrophages have a distinctive in vivo gene expression phenotype. *BMC Immunology* 2002; 3:7.
14. McNally A. K., K. M. DeFife, and J. M. Anderson. Interleukin-4-induced macrophage fusion is prevented by inhibitors of mannose receptor activity. *Am. J. Pathol.* 1996; 149, 975-985.
15. Murata T., J. Taguchi, R. K. Puri, and H. Mohri. Sharing of receptor subunits and signal transduction pathway between the IL-4 and IL-13 receptor system. *Int. J. Hematol.* 1999; 69, 13-20.
16. Namangala B., P. De Baetselier, W. Noel, L. Brys, and A. Beschin. Alternative versus classical macrophage activation during experimental African trypanosomosis. *J. Leukoc. Biol.* 2001; 69:387-396.
17. Pynaert G., P. Rottiers, A. Haegeman, S. Sehra, J. Korf, and J. Grooten. Antigen presentation by local macrophages promotes non-allergic airway responses in sensitized mice. *Am. J. Respir. Cell Mol. Biol.* 2003 (Epub ahead of print).
18. Raes G., P. De Baetselier, W. Noël, A. Beschin, F. Brombacher, and G. Hassanzadeh Gh. Differential expression of FIZZ1 and Ym1 in alternatively versus classically activated macrophages. *J. Leukoc. Biol.* 2002; 71:597-602.
19. Rodriguez-Sosa M., A. R. Satoskar, R. Calderon, L. Gomez-Garcia, R. Saavedra, R. Bojalil, and L. I. Terrazas. Chronic helminth infection induces alternatively activated macrophages expressing high levels of CCR5 with low interleukin-12 production and Th2-biasing ability. *Infect. Immun.* 2002; 70:3656-3664.
20. Suzuki N., K. Yamamoto, S. Toyoshima, T. Osawa, and T. Irimura. Molecular cloning and expression of cDNA encoding human macrophage C-type lectin. Its unique carbohydrate binding specificity for Tn antigen. *J. Immunol.* 1996; 156:128-135.
21. Tsuiji M., M. Fujimori, Y. Ohashi, N. Higashi, T. M. Onami, S. M. Hedrick, and T. Irimura. Molecular cloning and characterization of a novel mouse macrophage C-type lectin, mMGL2, which has a distinct carbohydrate specificity from mMGL1. *J. Biol. Chem.* 2002; 277:28892-28901.
22. Vanham G., L. Penne, H. Allemeersch, L. Kestens, B. Willems, G. van der Groen, K. T. Jeang, Z. Toossi, and E. Rich. Modeling HIV transfer between dendritic cells and T cells: importance of HIV phenotype, dendritic cell-T cell contact and T-cell activation. *Aids* 2000; 14, 2299-2311.

What is claimed is:

1. A method of marking alternatively activated macrophages, said method comprising:
   measuring an increase in gene expression level of macrophage galactose-type lectin (MGL) as a marker for alternatively activated macrophages.

2. The method according to claim 1, wherein said MGL is chosen from the group consisting of human MGL isoform 1, human MGL isoform 2, mouse MGL 1, and mouse MGL 2.

3. A method for marking alternatively activated macrophages, said method comprising:
   measuring an increase in galactose-type C-type lectin as a marker for alternatively activated macrophages.

4. The method according to claim 3, wherein said galactose-type C-type lectin is selected from the group consisting of human galactose-type C-type lectin isoform 1, human galactose-type C-type isoform 2, murine lectin galactose-type C-type lectin 1, and murine galactose-type C-type lectin 2.

5. A method of sorting alternatively activated macrophages, said method comprising:
   detecting a cell surface marker on alternatively activated macrophages so as to sort the alternatively activated macrophages, wherein said cell surface marker is a galactose-type C-lectin.

6. The method according to claim 5, wherein said cell surface marker is selected from the group consisting of human galactose-type C-type lectin isoform 1, human galactose-type C-type isoform 2, murine lectin galactose-type C-type lectin 1, murine galactose-type C-type lectin 2, and combinations of any thereof.

* * * * *